(12) United States Patent
Frost (10) Patent No.: US 7,610,641 B2
(45) Date of Patent: Nov. 3, 2009

(54) RESCUE DEVICE

(76) Inventor: Grant Frost, 4327 Ruth Crescent, North Vancouver, BC (CA) V7K 2N1

( * ) Notice: Subject to any disclaimer, the term of this patent is extended or adjusted under 35 U.S.C. 154(b) by 347 days.

(21) Appl. No.: 11/285,071

(22) Filed: Nov. 23, 2005

(65) Prior Publication Data

US 2006/0137097 A1   Jun. 29, 2006

Related U.S. Application Data

(60) Provisional application No. 60/630,207, filed on Nov. 24, 2004.

(51) Int. Cl.
  *A61G 1/013* (2006.01)
  *A61G 1/044* (2006.01)
  *A61G 7/10* (2006.01)
(52) U.S. Cl. .......................... 5/628; 277/625
(58) Field of Classification Search ............ 5/622, 5/628, 637, 625; 128/875
See application file for complete search history.

(56) References Cited

U.S. PATENT DOCUMENTS

| | | | | |
|---|---|---|---|---|
| 2,361,328 A | * | 10/1944 | Springer | 5/628 |
| 2,489,828 A | * | 11/1949 | Springer | 5/628 |
| 2,788,530 A | * | 4/1957 | Ferguson | 5/628 |
| 4,422,454 A | | 12/1983 | English | |
| 4,593,788 A | | 6/1986 | Miller | |
| 4,601,075 A | * | 7/1986 | Smith | 5/628 |
| 4,736,474 A | * | 4/1988 | Moran et al. | 5/627 |
| 5,014,374 A | * | 5/1991 | Williams | 5/628 |
| 5,083,574 A | * | 1/1992 | Schlutow | 5/628 |
| 5,211,186 A | * | 5/1993 | Shoemaker et al. | 5/628 |
| 5,435,323 A | * | 7/1995 | Rudy | 5/628 |
| 6,227,201 B1 | * | 5/2001 | Ferko, III | 128/869 |
| 6,966,087 B2 | * | 11/2005 | Robinette | 5/625 |
| 6,966,321 B2 | * | 11/2005 | Hess | 128/870 |
| 7,168,110 B2 | * | 1/2007 | Girard et al. | 5/89.1 |
| 2004/0088794 A1 | | 5/2004 | Calkin | |

FOREIGN PATENT DOCUMENTS

| CA | 2232406 | 11/1999 |
|---|---|---|
| CA | 2244113 | 2/2000 |

* cited by examiner

*Primary Examiner*—Jennifer H Gay
*Assistant Examiner*—Gilbert Y Lee
(74) *Attorney, Agent, or Firm*—Oyen Wiggs Green & Mutala LLP (57) ABSTRACT

A rescue device comprises a floating head support slidably attached to a back support. The rescue device can be incorporated into other rescue apparatus, such as a rescue harness. In one embodiment, the harness comprises a mantle for wrapping around a patient's arms and torso. The mantle is secured with chest straps connected across the patient's chest with a fastener. The mantle includes a pocket for holding back supports of various lengths. Leg straps form leg loops for the patient's legs. One or more lifting rings are attached to the harness for lifting the harness. The harness can also include a harness protector.

14 Claims, 13 Drawing Sheets

RESCUE DEVICE

CROSS-REFERENCE TO RELATED APPLICATION

This application claims the benefit of U.S. patent application No. 60/630,207 filed on 24 Nov. 2004 and entitled "Rescue Device", which is hereby incorporated herein by reference.

BACKGROUND

Previously, victims requiring rescue from confined spaces could be immobilized in a vest-type harness. U.S. Pat. No. 4,422,454, describes a vest-type harness for use in supporting victims while they are extricated from confined spaces. This vest-type harness includes a cervical collar, a lower body support adapted to encircle the lower back and chest of the victim, an upper body support adapted to overlie the upper back of the victim, and a head support adapted to overlie the back of the neck and at least a portion of the head of the victim. The vest-type harness includes chest straps for securing the lower body portion to the victim. Groin strap means are mounted to the outside surface of the lower body support and lie under the victims buttocks to prevent the harness from slipping. A single reinforcing stay extends vertically along the head support portion and lower body support to substantially immobilize the full length of the spine and head of the victim.

U.S. Pat. No. 4,593,788 also discloses a vest-type harness. This harness includes a padded head immobilizer and padded body vest, including a removable spine stiffener to immobilize the area around the spinal cord. The harness includes shoulder straps and groin straps to restrict movement of the harness on the victim. Lifting loops are attached to the harness for attaching a rescue line.

US Patent Application No. 2004/0088794 discloses an emergency stretcher. The stretcher has a single center base panel formed of a flexible sheet material. A pair of opposite, flexible, side torso flap members are arranged to be cinched against the sides of the torso of a victim to secure the victim to the stretcher. The stretcher may be used for dragging a victim from an injury site.

There is a need for an improved rescue devices.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

This invention relates to rescue devices. Rescue devices according to the invention may be used to extricate patients from confined spaces. Such devices can be particularly useful in vertical extrications. In one embodiment, the rescue devices are incorporated into a rescue harness. Other applications of the device will be apparent to persons skilled in the art.

In one embodiment, the device comprises a floating head support slidably attached to a back support. The floating head support also comprises one or more straps for securing a patient's head to the head support. The rescue device can comprise straps for securing the patient to the back support. Once the patient is secured to the device, the floating head support allows a patient's head to float within the rescue device, even when the patient is moved from a horizontal position to a vertical position, and vice versa. In another embodiment of the invention, rescue device comprises straps for securing a patient to a harness or other rescue apparatus. In another embodiment, the rescue device comprises a harness protector to protect harnesses from abrasion.

In one embodiment of the invention, the rescue devices are incorporated as part of a rescue harness. The harness comprises a mantle adapted for wrapping around a patient's arms and torso, a pocket in the mantle for carrying the back support to protect the patient's spine, one or more straps attached to the mantle for attaching means to lift the harness, and chest straps for securing the mantle around the patient's arms and torso and securing the back support to the patient. The chest straps are attached to the mantle and secured to one another across the patient's chest with a fastener. Because the chest straps are secured to one another across the patient's chest, the straps do not move up against the patient's throat and head, nor do the straps slip down towards the patient's waist.

The harness also comprises leg straps which attach to the mantle to form leg loops. The harness optionally includes a removeable harness protector which is adapted to attach to the back of the harness to protect the harness from abrasion.

The back support can be adapted to be inserted into the pocket of the mantle of the harness, the back support comprising means for slidably attaching the head support to the back support. The head support has straps for securing the patient's head in the head support. The head support can slide freely, or float, longitudinally along the back support.

In other embodiments of the invention, the floating head support, chest straps, and harness protector can be adapted for use with other harnesses and rescue apparatuses. For example, the floating head support is particularly useful with other harnesses, back supports, and rescue apparatuses, such as a rescue basket, which are used to vertically extricate a patient, since the floating head support can help to reduce strain and discomfort on a patient's head, neck, and spine when the patient is moved from a horizontal to a vertical position, and vice versa. The chest straps can be used with any other harnesses, back supports, and rescue apparatuses to more soundly secure a patient, particularly in situations where the patient must be moved into different positions, including vertical, horizontal, or lateral positions, in order to be extricated. The harness protector is particularly useful to protect harnesses that are used in environments which are abrasive.

Further details of the invention and features of specific embodiments of the invention are described herein.

BRIEF DESCRIPTION OF DRAWINGS

In drawings which illustrate embodiments of the invention and which are intended to be construed in an illustrative rather than a restrictive sense.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

In the field of rescue, it was previously thought that effective spinal immobilization could be accomplished by splinting a patient's spine, neck and head. This has influenced many prior art harness designs. However it is now well known in the field of medicine that spinal stabilization can only truly be accomplished by means of head-to-toe immobilization. However, in many rescue situations, including confined space rescues, or rescues requiring vertical extrication of a patient, it is not physically or temporally possible to perform these types of immobilization procedures. In some situations, it is prudent to effect minimally required patient stabilization and remove the patient from an unsafe environment to an area where, if necessary, full body immobilization can be implemented. In certain situations, including situations where a patient must be moved from a horizontal to a vertical position, and vice versa, it is also important to address the discomfort, tension, or even injury that may occur to the patient's neck and spine if the position of the patient's head relative to the patient's body is not allowed to adjust within the harness apparatus when the patient is moved from a horizontal position to a vertical position, and vice versa.

The invention relates to rescue devices. In one embodiment, the rescue device comprises a floating head support slidably attached to a back support. The floating head support comprises one or more straps for securing the patient's head. The back support may comprise straps for securing a patient to the back support. In another embodiment, the rescue device comprises straps for securing a patient to a harness or other rescue apparatus. The straps can be attached to the harness or other rescue apparatus and are attached across the patient's chest to secure the patient to the harness or rescue apparatus. In another embodiment, the rescue device comprises a harness protector to protect harnesses from abrasion.

The rescue devices can be incorporated into a number of different rescue apparatuses which would be apparent to a person skilled in the art, including a rescue harness. One such embodiment of a rescue harness is described herein.

The rescue harness of one embodiment of the invention can be used for vertical rescues, particularly from confined spaces. However, the harness can also be used in other rescue situations which would be appreciated by a person skilled in the art. For example, the rescue harness can be adapted for rescuing patients from steep or high angle locations and confined space environments such as found in crane towers, barges, tanks, collapsed structures, or crevices. The harness can also be used for rescuing patients where the patient is in a sitting position in a restricted space, such as in a vehicle.

The harness can be wrapped over the patient's arms and torso, effectively immobilizing, controlling, and protecting the patient's upper body. The harness provides a narrow patient profile while protecting the patient. Spinal protection is provided by a rigid back support that will not flex when the harness is dragged over an unsupported edge. The harness of the invention is simpler to apply than prior art harnesses, as it requires fewer straps to secure the patient in the harness. Head stabilization is achieved by securing the patient's head to a head support with detachable straps. An optional hard collar can also be applied. The harness can also comprise a harness protector for protecting the harness against abrasion.

Figure 1:
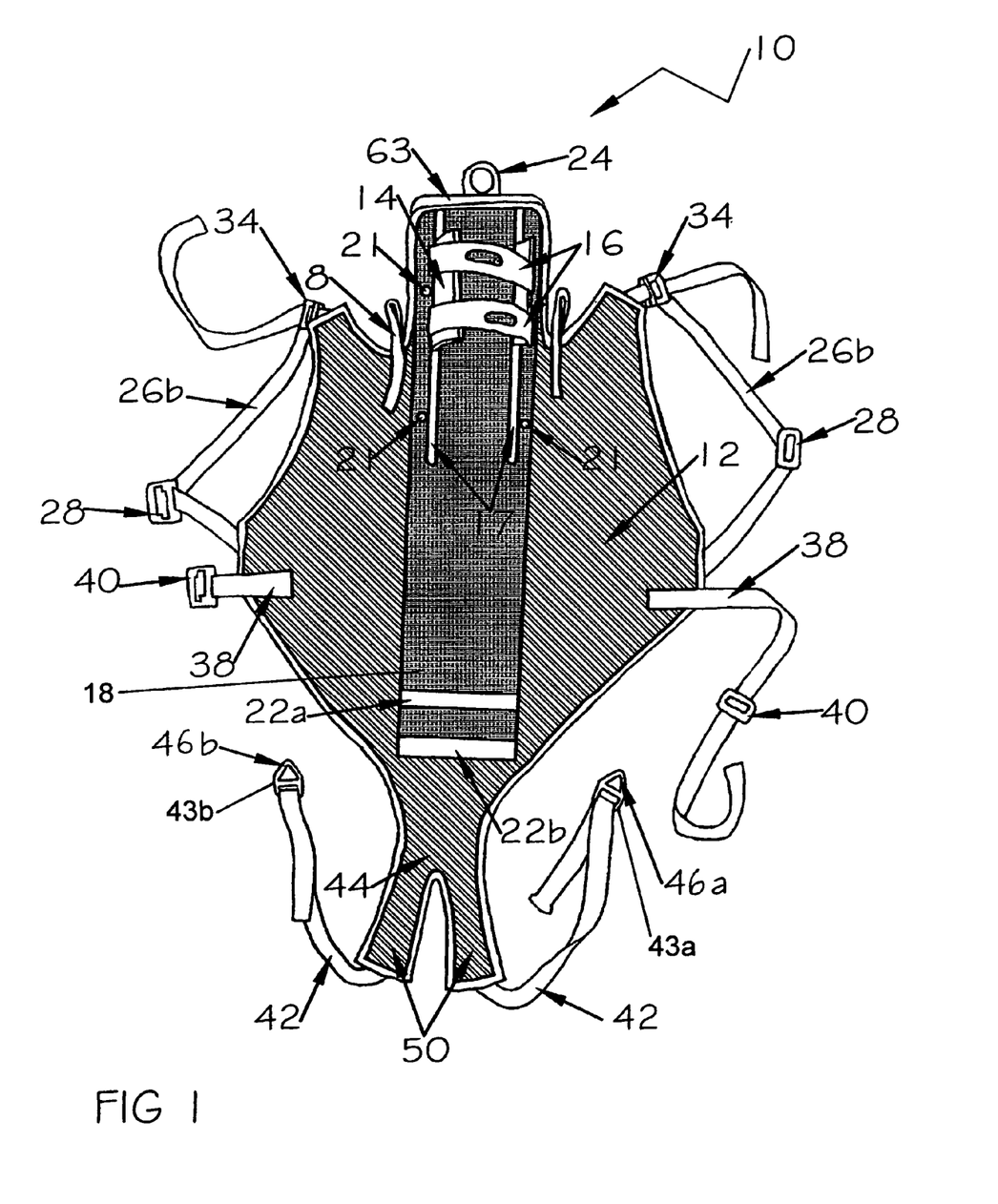
FIG. 1 is a front view of a rescue harness according to one embodiment of the invention.

FIG. 1 is a front view of a rescue harness 10 in a laid-open configuration. Rescue harness 10 comprises a mantle 12 made of a durable, flexible material, such as nylon. Other suitable materials may also be used for mantle 12. The harness also includes a head support 14 for holding a patient's head which includes straps 16 for immobilizing the head.

Figure 3:
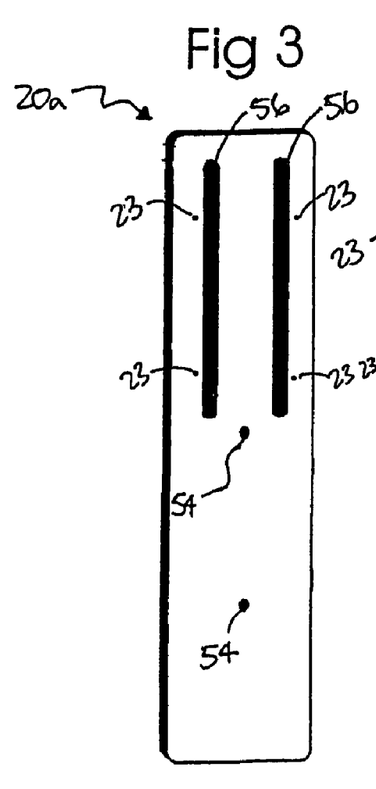
FIG. 3 is front isometric view of the back support according to one embodiment of the invention.
Figure 4:
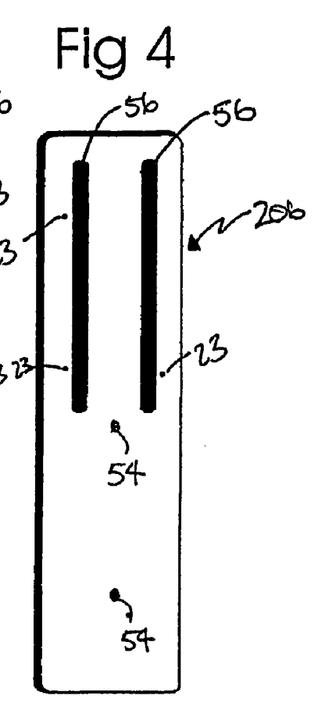
FIG. 4 is front isometric view of the back support according to another embodiment of the invention.

Mantle 12 comprises a pocket 18, which is oriented generally vertically along the length of mantle 12. Pocket 18 can receive a back support 20 for supporting a patient's spine. Pocket 18 includes one or more closures 22, such as a flock and loop closure or other suitable closure, which allows back support 20 to be easily removed and inserted. Closures 22a and 22b are located at different lengths along pocket 18. This allows back supports of different lengths, as illustrated in FIGS. 3 and 4, to be inserted into pocket 18. Shorter back supports, such as back support 20b shown in FIG. 4, can be used, for example, with patients who must be immobilized in a sitting position. Mantle 12 can also comprise one or more slots 17, which allow head support 14 to pass through the top surface of pocket 18 and attach to back support 20. As will be described later, straps 16 are attached to head support 14 and used to immobilize the patient's head in head support 14. Fasteners 21 on mantle 12 can be used to additionally secure mantle 12 to back support 20 by attaching to fastener receivers 23 of back support 20. Such fasteners 21 can be snap fasteners or other fasteners known to persons skilled in the art.

Figure 2:
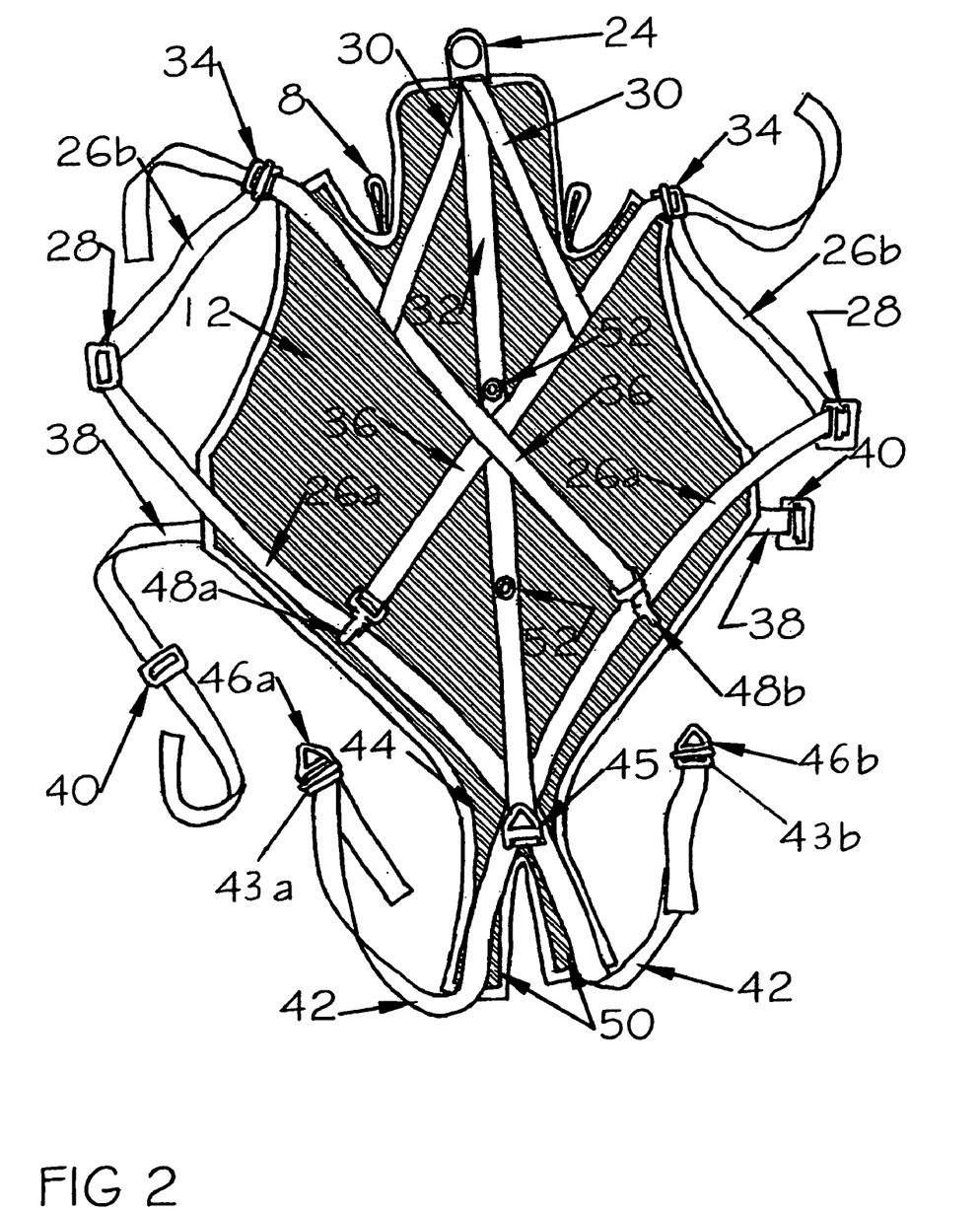
FIG. 2 is a back view of a rescue harness according to one embodiment of the invention.

A lifting ring 24 to which a rescue line can be attached is located on the top of harness 10. Lifting ring 24 is made of a strong material, such as metal, which is capable of carrying a load. As illustrated in FIG. 2, which is a back view of an embodiment of harness 10, lifting ring 24 can be attached to reinforcement straps 30, which are sewn into or otherwise attached to mantle 12 and centre strap 32, which is also sewn into or otherwise attached to mantle 12 along the vertical length of mantle 12. Such straps bear the weight of the patient when a patient is being lifted in the harness. When a patient is securely strapped into the harness, the patient can be vertically lifted by attaching a rescue line to lifting ring 24. Although it is disclosed that lifting ring 24 is attached to centre strap 32 and reinforcement straps 30, other suitable strapping configurations could also be used to attach lifting ring 24. Such configurations would be known to persons skilled in the art. It is contemplated that all straps of harness 10 are made from continuous pieces of webbing, but may also be made from separate pieces of strapping material sewn together or otherwise integrated together.

The arms and torso of a patient can be strapped into rescue harness 10 by wrapping mantle 12 around the patient's arms and torso and securing mantle 12 across the patient's chest by attaching chest straps 26 to each other using floating fastener 28. As illustrated in FIG. 2, chest straps 26a are sewn into or otherwise attached to mantle 12, extending from center strap 32, near y-shaped tail 44, and generally following the lower outside edge of mantle 12. Such a configuration of chest straps 26a helps maintain structural integrity between the straps and mantle 12, and to facilitate wrapping of a patient. However, chest straps 26a can also be sewn into or otherwise attached to mantle 12 in other suitable configurations to facilitate the wrapping of harness 10 around a patient.

Chest straps 26b, which are the portions of chest straps 26 which are not attached to mantle 12, are adjustable to ensure a secure fit of harness 10 around the patient. The ends of chest straps 26b are threaded through chest strap buckles 34, which allow the straps to be easily adjusted and tightened across the patient's chest. The ends of chest strap 26b on each side of harness 10 can be threaded through the chest strap buckle 34 which is located on the same respective side of the harness 10, thereby forming a loop on each side of harness 10. The ends of chest straps 26b can be treaded through buckles 34. Chest strap buckles 34 are attached to the ends of reinforcement straps 36, which are sewn into or otherwise attached to mantle 12 in a generally crisscross configuration across the back of mantle 12 to maintain structural integrity between the straps and mantle 12. Other suitable configurations for attaching reinforcement straps 36 to mantle 12 are known to persons skilled in the art. It is also contemplated that chest strap buckles 34 can be attached to portions of mantle 12.

Chest straps 26b can be connected to one another and secured across the front of a patient with floating fastener 28, which can comprise male and female quick connect fasteners, or other suitable fasteners. For example, one portion of floating fastener 28 can be attached to chest strap 26b on one side of the harness and another portion of floating fastener 28 can be attached to chest strap 26b on the other side of the harness, and the two portions are detachably affixable to one another.

Floating fastener 28 holds chest straps 26b in place across the patient's chest. Because each of the chest straps does not crisscross the patient's chest, and because the chest straps are secured to one another across the front of the patient's chest with floating fastener 28, this prevents the straps from sliding up against the patient's throat and head, which can cause discomfort or injury by choking the patient. The position of floating fastener 28 is adjustable along the lengths of chest straps 26b. This allows harness 10 to be used with patients of varying heights and sizes.

Figure 10:
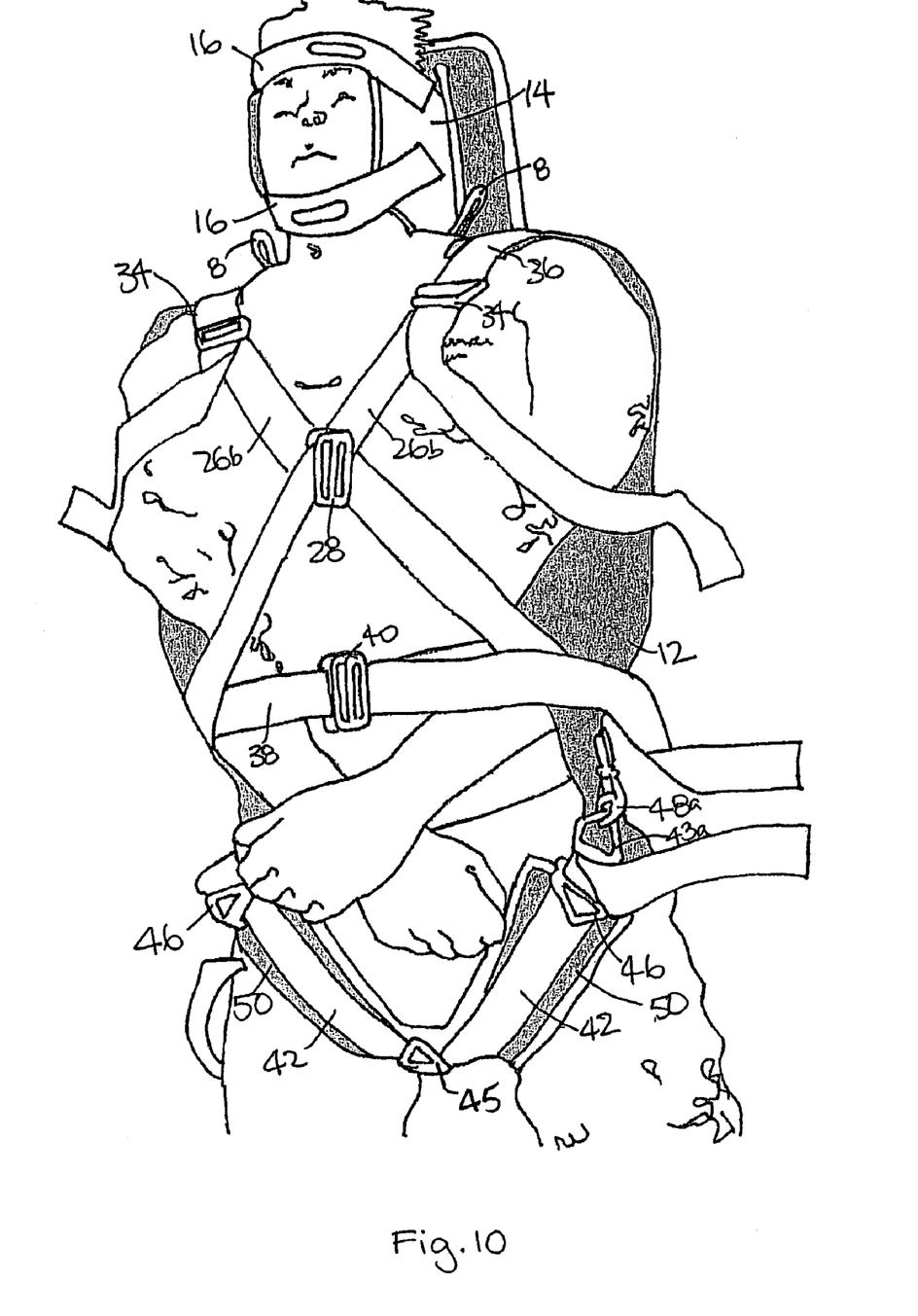
FIG. 10 is a front isometric view of a patient secured into the rescue harness according to one embodiment of the invention.

In another embodiment of the invention, chest straps 26b can be criss-crossed across the patient's chest as illustrated in FIG. 10. The ends of each chest strap 26b can be connected to chest strap buckles 34 located on the opposite side of the patient's chest. In such embodiments, a separate fastener may be attached to chest straps 26b at their crossing point on the patient's chest to prevent the straps from sliding up against the patient's throat and head.

It is contemplated that chest straps 26 and floating fastener 28, or criss-crossed chest straps 26 fastened at the crossing point can be adapted for use with other harnesses or rescue systems, which may or may not have mantles. For example, this system could be adapted for use in splinting a patient to a half- or full-body back support, or for use in securing a patient in a basket stretcher, or any other system which requires a patient to be secured into a rescue apparatus across the chest. By securing chest straps 26 across the patient's chest, the straps do not move, which allows patients of different sizes, including children, to be secured to different rescue apparatuses.

Referring back to harness 10, the harness also includes waist strap 38, which is sewn into or otherwise attached inside mantle 12. Waist strap 38 can be wrapped around the waist and arms of a patient, and the ends of waist strap 38 are attached to, or inserted through, waist fasteners 40, which are used to secure waist strap 38 around the patient. Waist strap 38 can be tightened around the patient by adjusting the position of waist fasteners 40 along waist strap 38.

Harness 10 can also include straps 8, which are sewn into or otherwise attached to mantle 12 and straps 36, near the top of mantle 12 where the patient's shoulders would generally be located, and which can be used by rescue personnel to lift a patient.

The bottom portion of harness 10 comprises leg straps 42, which are sewn into or otherwise attached to the y-shaped tail 44 of mantle 12. Leg strap buckles 43 are attached to the ends of leg straps 42 which can attach to leg strap connectors 48. Leg strap connectors 48 are attached to the ends of reinforcement straps 36 discussed above. Leg straps 42 and y-shaped tail 44 form leg loops for the patient's legs, as shown in FIG. 10, when leg strap buckle 43a is attached to leg strap connector 48a, which is located on the same lateral side of harness 10 as leg strap buckle 43a, and leg strap buckle 43b is attached to leg strap connector 48b, which is located on the same lateral side of harness 10 as leg strap buckle 43b. When leg strap buckles 43 of leg straps 42 are connected to their respective leg strap connectors 48, y-shaped tail 44 and leg straps 42 pass under the buttocks and between the legs of the patient. Leg strap buckles 43 also comprise lifting rings 46 to assist in lifting a patient. For example, lifting rings 46 can be used to lift a patient horizontally while making a transition over an edge or when there is the need to horizontally suspend the patient during extrication.

Leg straps 42 are sewn into or otherwise attached to the mantle along each branch 50 of y-shaped tail 44. When the patient is secured in the harness and the patient is lifted in an upright position, leg straps 42 and y-shaped tail 44 supports the weight of the patient being lifted in harness 10. The size of the leg loops formed by leg straps 42 can be adjusted by moving the position of leg strap buckles 43a and 43b along the length of leg straps 42 as necessary. Y-shaped tail 44 may include padding to help prevent the harness from unduly applying pressure against the patient's legs and buttocks when a patient is being lifted in the harness.

Figure 9:
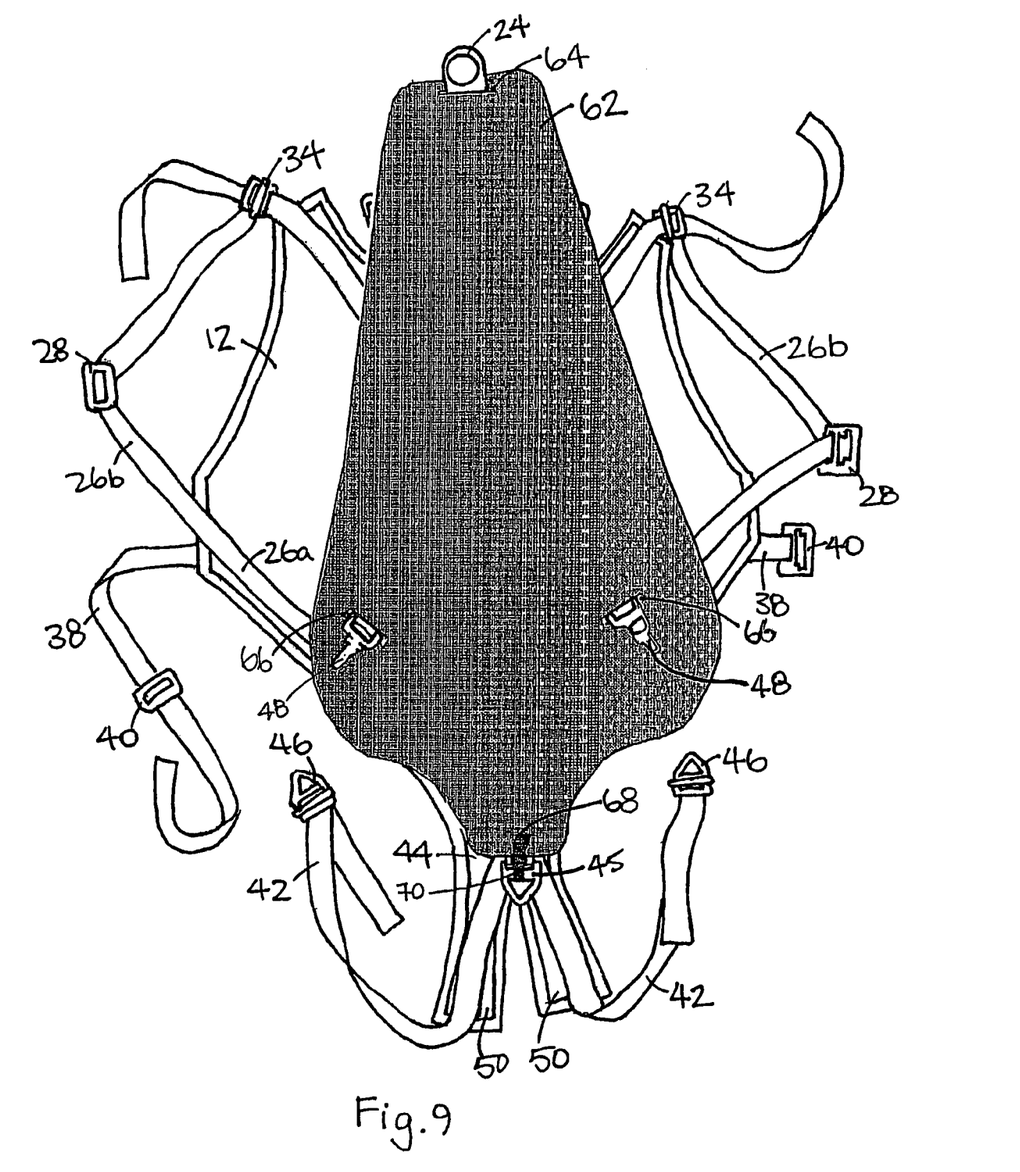
FIG. 9 is a bottom view of the harness protector according to another embodiment of the invention attached to a harness.

Lower lifting ring 45, as shown in FIGS. 2, 9, and 10, is located near Y-shaped tail 44 and is attached to center strap 32 and chest straps 26a. Ropes or rescue lines can be attached to lower lifting ring 45 to "tag" the patient or direct the patient away from obstructions when raising or lowering the patient during a rescue. Lower lifting ring 45 can also be used to attach a rescue line if it is necessary to pull the patient out of a confined space feet first or if it is necessary to lower the patient head first.

As previously discussed, centre strap 32 is sewn into or otherwise attached generally along the centre of the back of harness 10 and crosses all other straps. Centre strap 32 supports the weight of the patient when the harness is lifted from lifting ring 24, attached near the top of harness 10, or lower lifting ring 45 attached near the bottom of harness 10. Centre strap 32 includes grommet holes 52 for accessing bolting points 54, which are built into back support 20, as illustrated in FIGS. 3 and 4. Bolts can be applied through grommet holes 52 into bolting points 54 of back support 20 to secure harness protector 63 to mantle 12 and back support 20. The bolts can be secured with nuts, although other fasteners, such as self tapping threaded bolt inserts are contemplated. Other types of fasteners are readily known to persons skilled in the art. Preferably, fasteners for attaching harness protector 63 to harness 10 are removable to allow harness protector 63 to be easily removed from harness 10 or to allow back support 20 to be quickly removed from harness 10 and changed with a back support having a different length, if necessary.

Back support 20 is constructed to be slightly smaller than pocket 18, so that back support 20 can slide easily into pocket 18. Different lengths of back supports 20 can be used with the rescue device of the invention, as illustrated by back support 20a in FIG. 3, and back support 20b in FIG. 4. As discussed above, pocket 18 can comprise multiple closures 22a and 22b located at the bottom of pocket 18, for enclosing back supports of different lengths. A back support 20 of an appropriate length can be selected to adapt the harness to particular rescue situations. For example, a shorter back support 20 can be used for rescues in confined spaces having restricted head room. A shorter back support 20 can also be used with a shorter patient, such as a child. Therefore, harness 10 can be quickly and easily adapted for use in different rescue situations.

Harness 10 also comprises head support 14. Head support 14 is slidably attached to back support 20 and slides longitudinally along back support 20 without rotation.

Figures 5, 6:
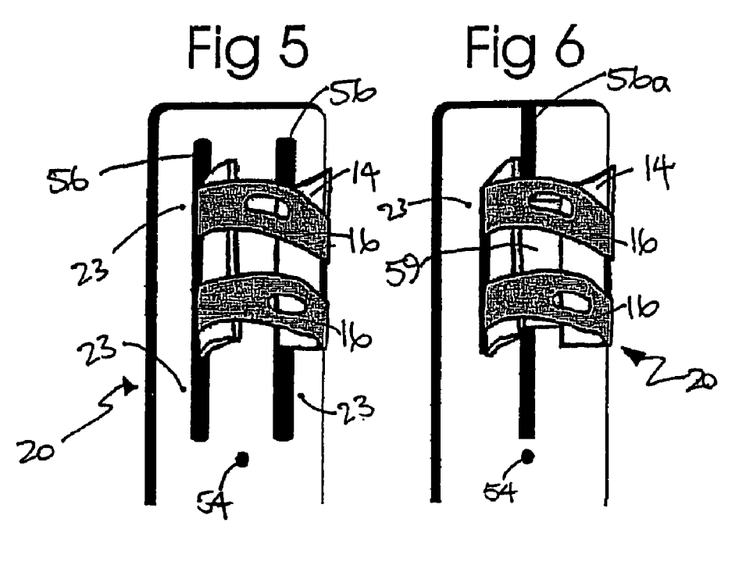
FIG. 5 is front isometric view of the head support according to one embodiment of the invention.
FIG. 6 is a front isometric view of the head support according to another embodiment of the invention.
Figure 5A:
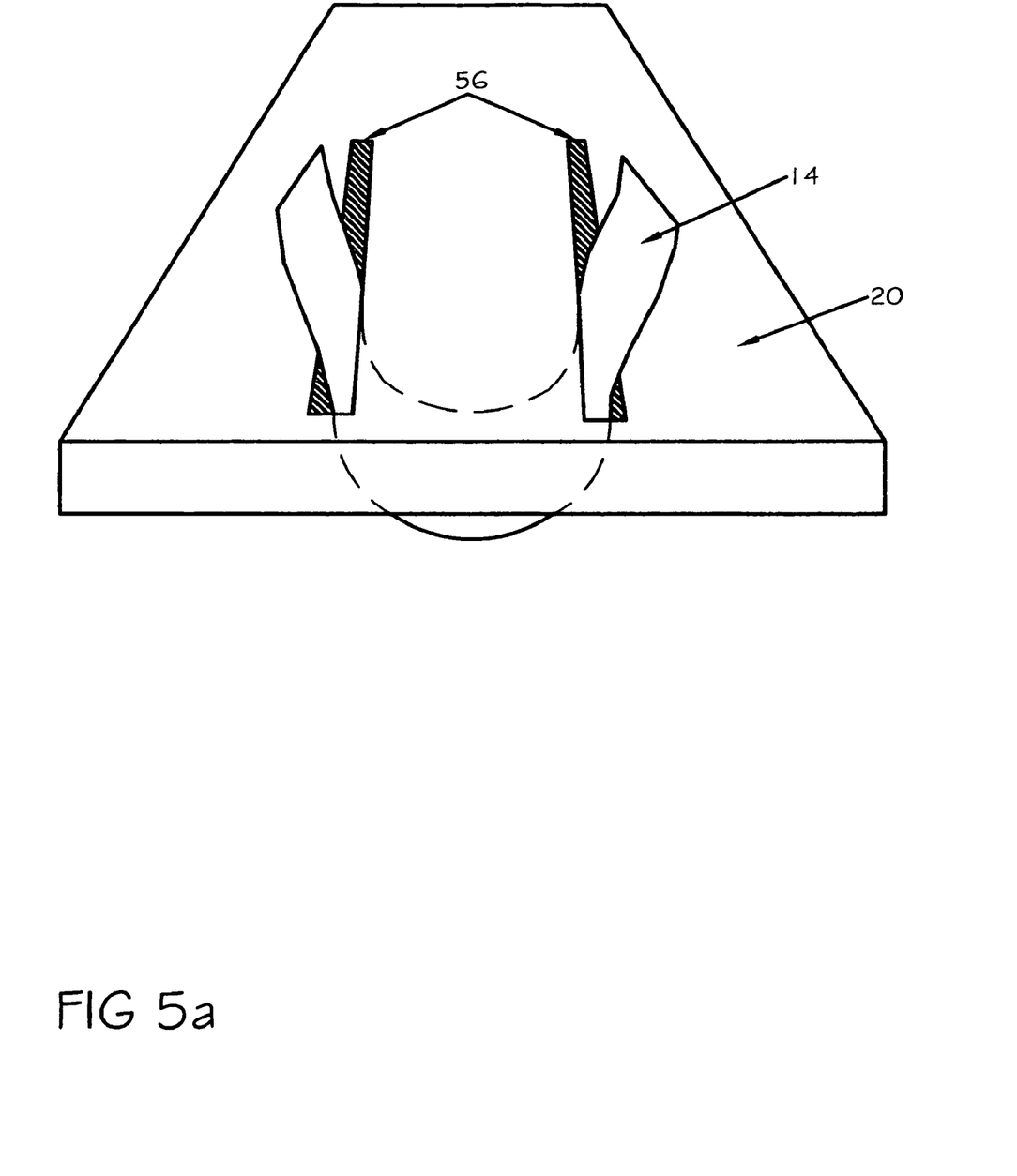
FIG. 5a is an end perspective view of the head supporting according to one embodiment of the invention.

FIGS. 3, 4, 5, 5a, 6, 11, 12, and 14 illustrate examples of mechanisms for slidably attaching head support 14 to back support 20. As shown in FIGS. 5 and 6, back support 20 can comprise one or more head support tracks 56. Head support tracks 56 receive head support 14. In one specific embodiment, wherein back support 20 comprises two head support tracks 56 as shown in FIGS. 3 and 5, head support 14 can be inserted through tracks 56 and looped around the back of backboard 20 to secure a patient's head to back support 20, as shown in FIGS. 5 and 5a.

Figure 11:
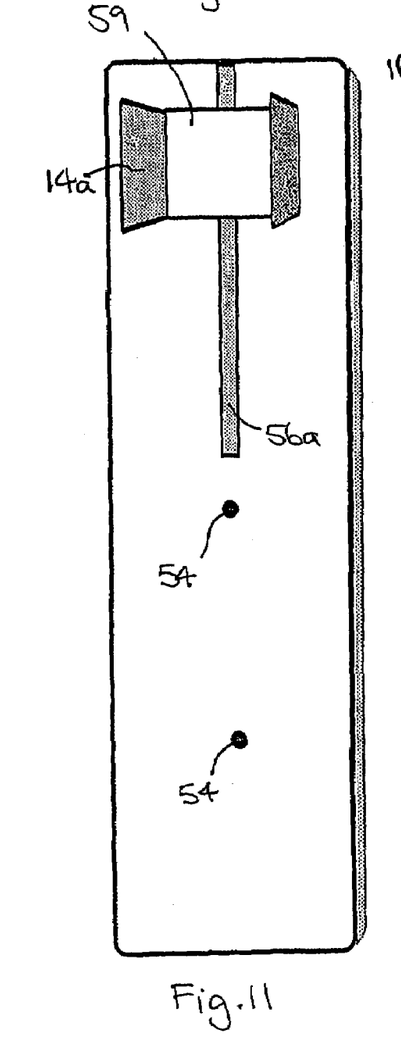
FIG. 11 is top isometric view of the head support attached to the back support according to one embodiment of the invention.
Figure 12:
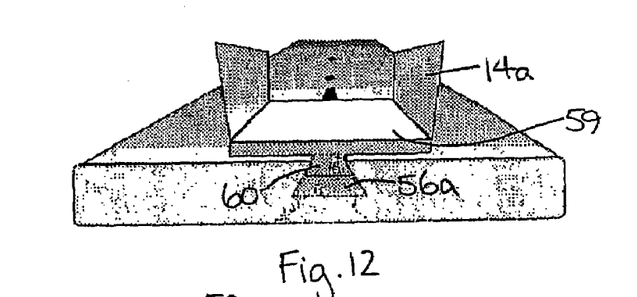
FIG. 12 is an end perspective view of the head support attached to the back support according to one embodiment of the invention.
Figure 13:
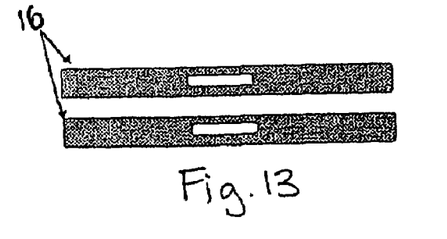
FIG. 13 is a top view of the head straps of the head support according to one embodiment of the invention.
Figure 14:
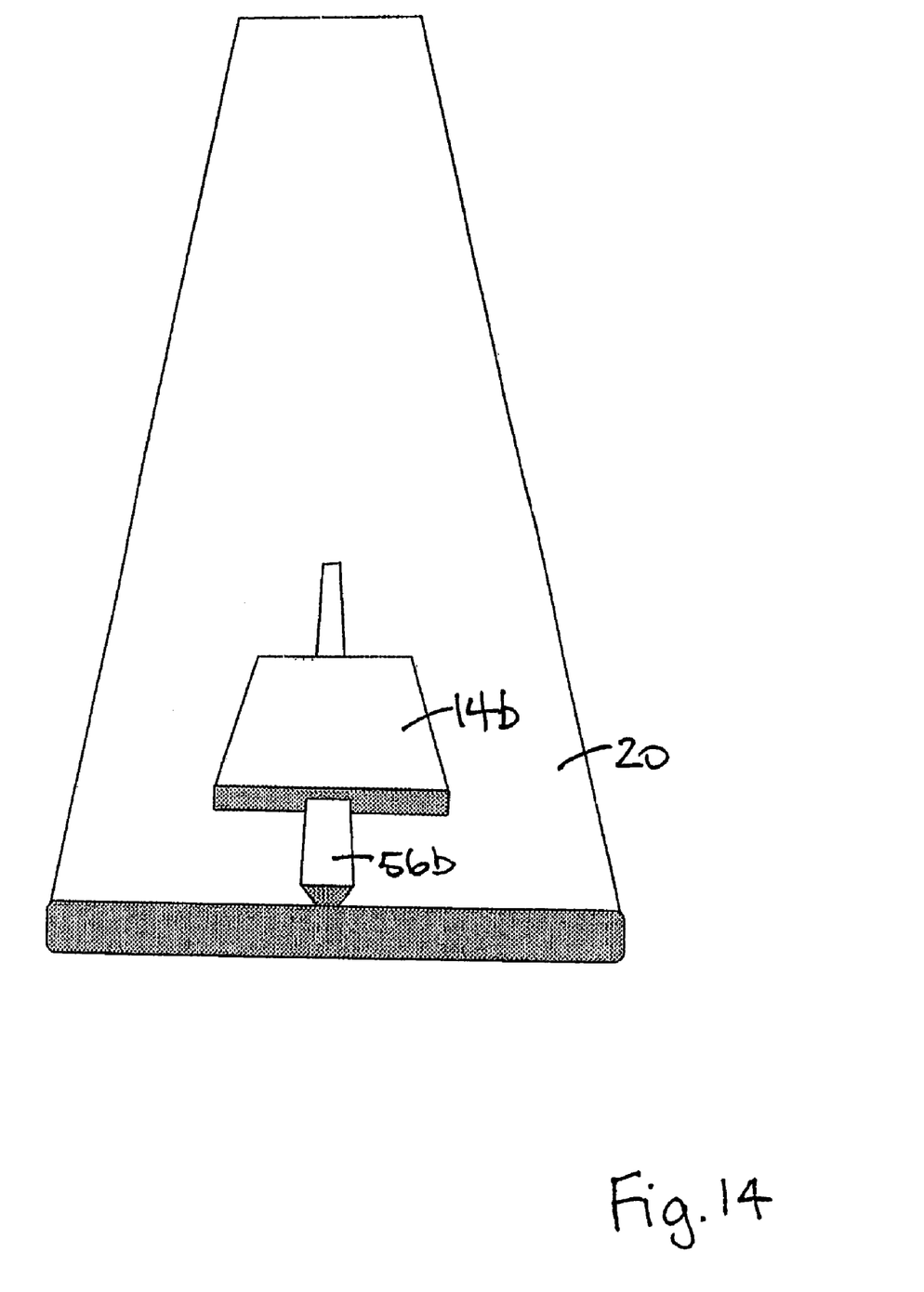
FIG. 14 is an end perspective view of a head support attached to the back support according to another embodiment of the invention.

FIGS. 6, 11, 12, and 14 illustrate other embodiments of the mechanism for slidably attaching head support 14 to back support 20. As shown in FIG. 6, back support 20 can comprise a single head support track 56a for accommodating a floating head support 14a. FIG. 12 illustrates one specific embodiment wherein floating head support 14a is inserted into single head support track 56a. In FIGS. 11, 12, and 14, straps 16 have been omitted for clarity. Straps 16 are illustrated in FIG. 13. As shown in FIG. 12, head support track 56a is adapted in shape to receive projecting member 60, which is attached to backing 59 of floating head support 14a. Head support track 56a and projecting member 60 can be made from low friction materials, such as plastic which allow floating head support 14a to freely slide up and down head support track 56a. Projecting member 60 can comprise any shape which allows floating head support 14a to move along the longitudinal axis of head support track 56a, and which holds floating head support 14a within head support track 56a. Backing 59 and straps 16 may be padded to cushion the patient's head.

FIG. 14 illustrates another specific embodiment wherein head support track 56b is raised relative to the surface of back support 20. In this case, head support 14b comprises a notch for receiving head support track 56b. Head support track 56b can comprise any shape which head support 14b can receive and which allows head support 14b to slide longitudinally along back support 20.

Other methods of slidably attaching head support 14 to back support 20 are contemplated. For example, head support 14 and back support 20 may each comprise tracks in which a third attachment means may be inserted to connect head support 14 and back support 20 together. Head support 14 may also be configured to fit within a groove in back support 20. These and other methods of slidably attaching head support 14 to back support 20 are known to persons skilled in the art.

When a patient's head is strapped into floating head support 14, the patient's head can move freely along the length of back support 20 within the length of head support track 56, as dictated by the movement of the patient's body, which may reduce discomfort and harm to the patient. For example, when a patient is moved from a horizontal position to a vertical position, gravity draws the body downwards. If a patient's head is secured to a head support which does not allow the head to move, the weight of the patient's body will pull on the patient's neck, head and spine. Harness 10 with floating head support 14 slidably attached to back support 20 allows the patient's head to move with gravity when being moved from a horizontal to a vertical position, and vice versa, while the head remains secured and supported against rotation or twisting in the harness. In addition, a neck collar can also be attached to the patient to provide additional neck support.

Although in one embodiment it is disclosed that floating head support 14 is used as part of rescue harness 10, it is contemplated that floating head support 14 can be used with other rescue apparatuses. In one such embodiment, floating head support 14 can be used with a trauma board. Floating head support 14 and back support 20 may also be used with rescue cages for air-lifting a patient. Floating head support 14 can also be used in association with cervical boards rather than full length back supports, to affect rescues from confined spaces. Floating head support 14 can be adapted for use with many other types of rescue devices, particularly rescue devices involved in vertical extrication of patients which would be appreciated by a person skilled in the art.

FIG. 10 illustrates correct patient positioning in harness 10, with the patient lying supine with his head centered in head support 14, secured by straps 16.

FIG. 9 illustrates a harness protector 62 which may be integrated with harness 10. Harness protector 62 comprises a lifting ring slot 64 for accommodating lifting ring 24, and leg strap connector slots 66 for accommodating leg strap connectors 48. A strap 70, or other suitable fastener, is inserted through lower slot 68 for attaching harness protector 62 to lower lifting ring 45 at the base of y-shaped tail 44. Although it is disclosed in this embodiment that harness protector 62 is attached to harness 10 in a specific manner, many other configurations for attaching harness protector 62 to harness 10 or any other suitable harness in need of abrasion protection are also contemplated and would be appreciated by a person skilled in the art.

Figure 15:
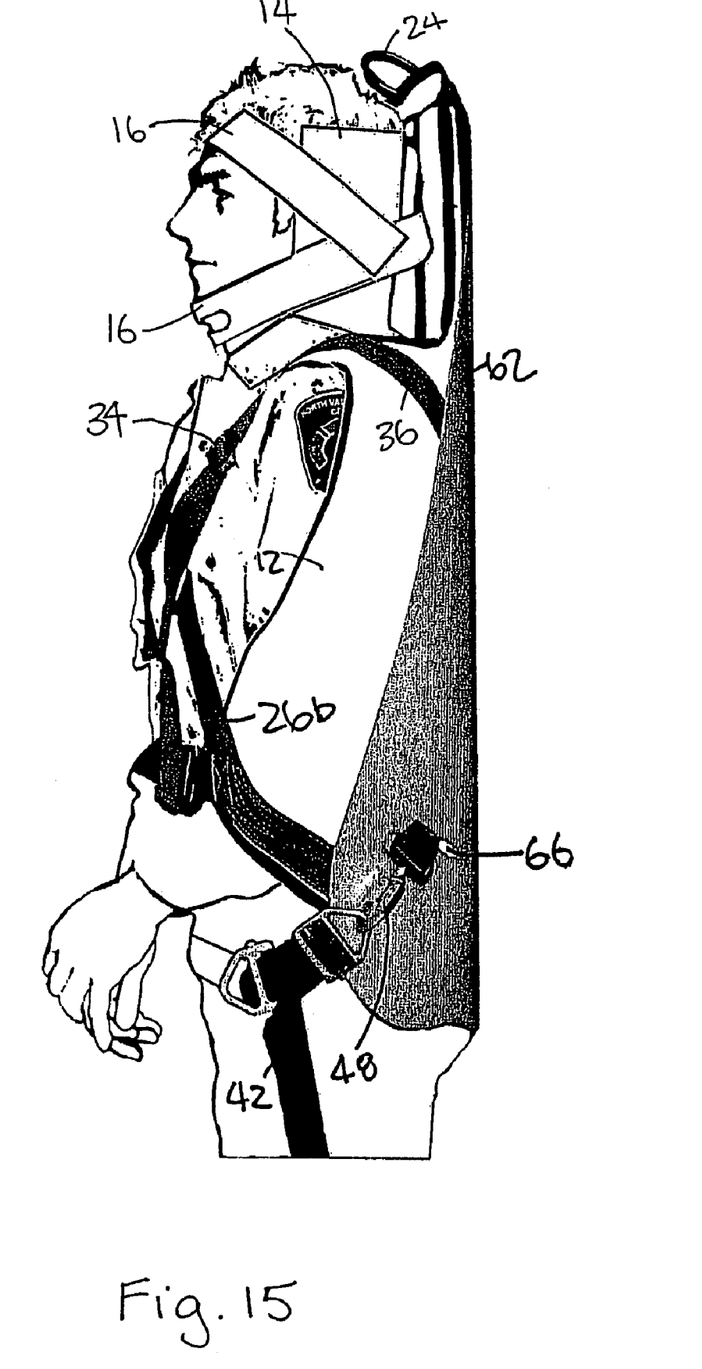
FIG. 15 is a side view of a patient secured to the rescue harness with the harness protector according FIG. 9 attached to the harness.
Figure 16:
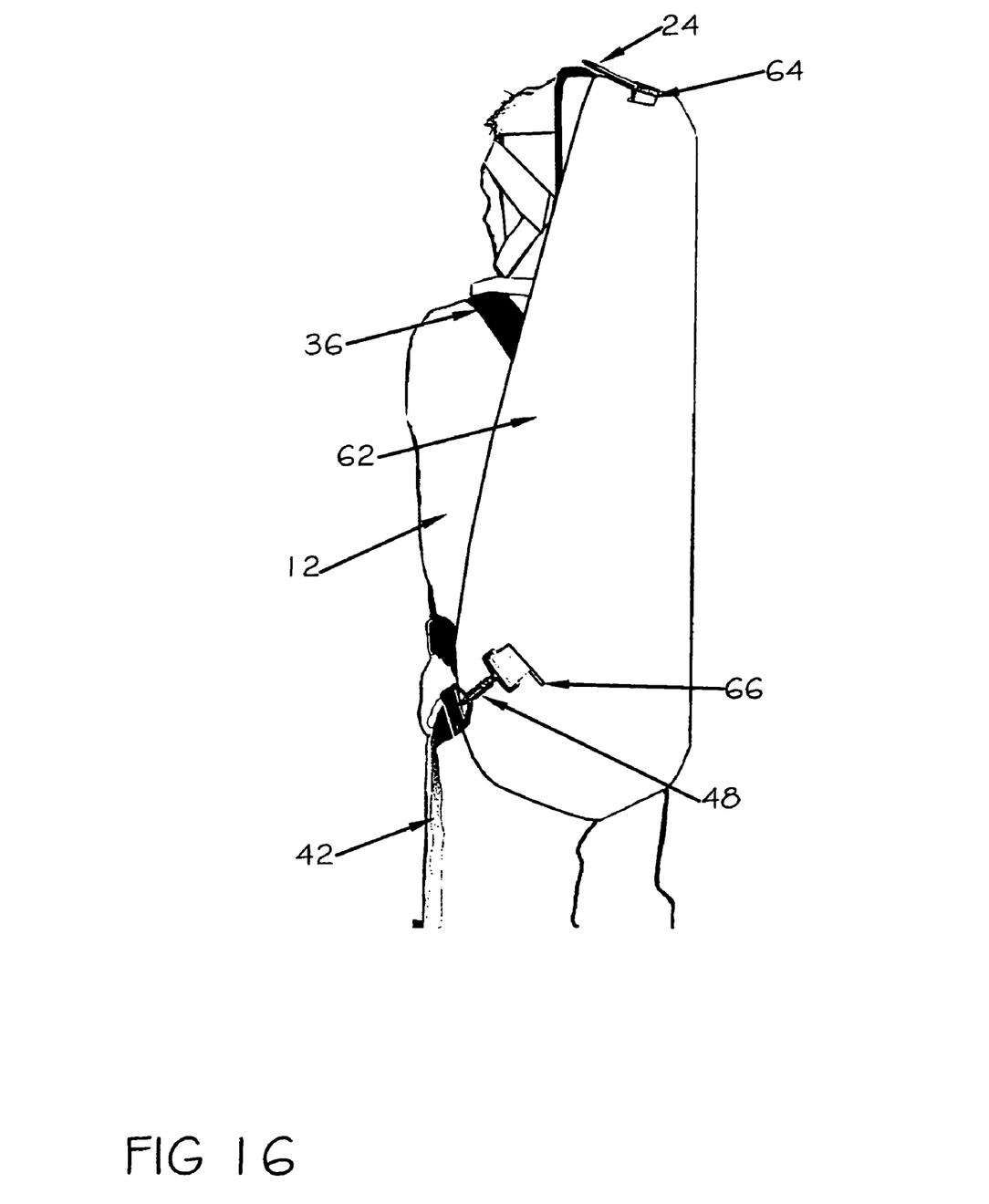
FIG. 16 is a partial side and back view of a patient secured to the rescue harness with the harness protector according to FIG. 9 attached to the harness.

As illustrated in FIGS. 15 and 16, harness protector 62 has a profile generally similar to the profile of a patient secured into harness 10, so that the patient maintains a slim profile which can aid rescue from confined spaces. Harness protector 62 protects the back and sides of harness 10 from abrasion. Moreover, because harness protector 62 is attached to lower lifting ring 45 of harness 10, which is generally located between the legs of the patient, harness protector 62 provides increased support under the patient's buttocks when the patient is being vertically lifted, thereby increasing the comfort of the patient. Because harness protector 62 curves into the patient's buttocks and between the patient's legs when it is attached to harness 10, harness protector 62 has a smooth profile, which allows harness protector 62 to slide easily over surfaces without catching obstructions or protrusions which may hinder a rescue.

Harness protector 62 can be made from a durable plastic, or other suitably abrasion-resistant material to protect the harness from abrasion during rescues. Harness protector 62 does not need to be changed when harness 10 is used with back supports 20 of different lengths, since harness protector 62 is flexible and conforms to the profile of harness 10. Harness protector 62 does not need to be removed from harness 10. Therefore, harness 10 can always be protected from abrasion and valuable time and energy is not expended during a rescue to secure harness protector 62 to harness 10. When harness protector 62 requires replacement due to overuse, it can be replaced cheaply and quickly without the expense of replacing the entire rescue harness.

Figure 7:
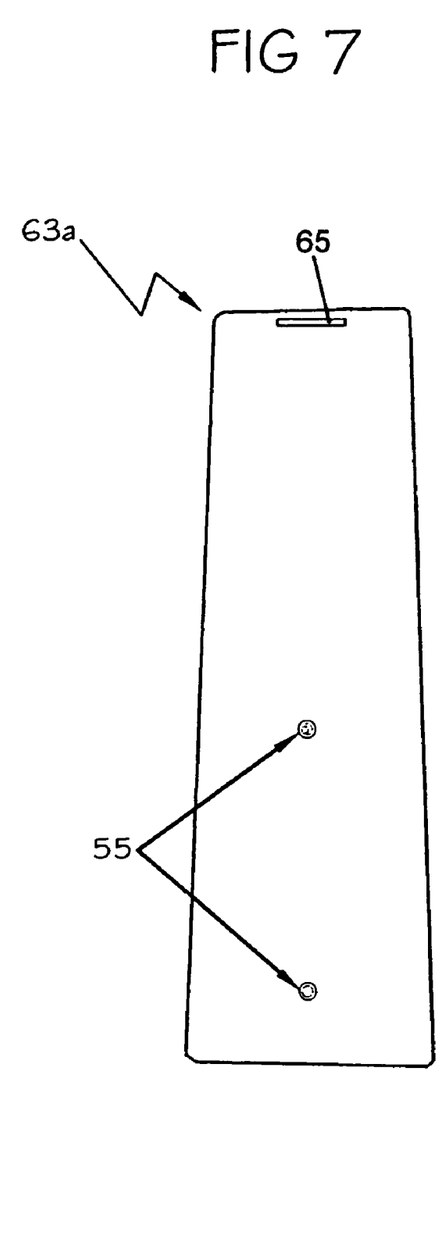
FIG. 7 is a back view of the harness protector according to one embodiment of the invention.
Figure 8:
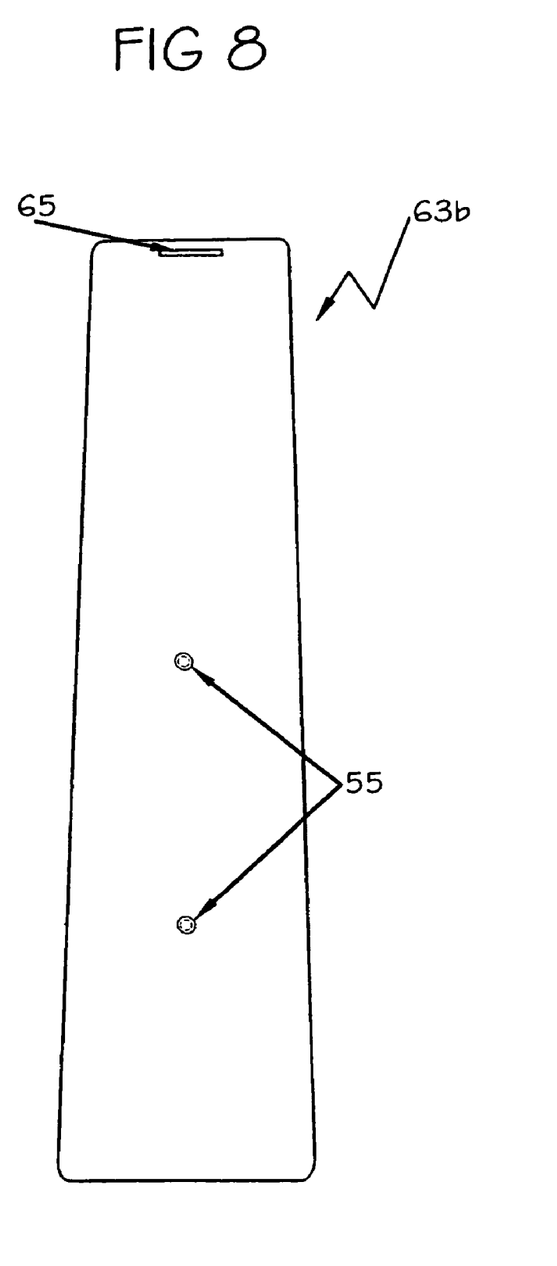
FIG. 8 is a back view of the harness protector according to another embodiment of the invention.
Figure 17:
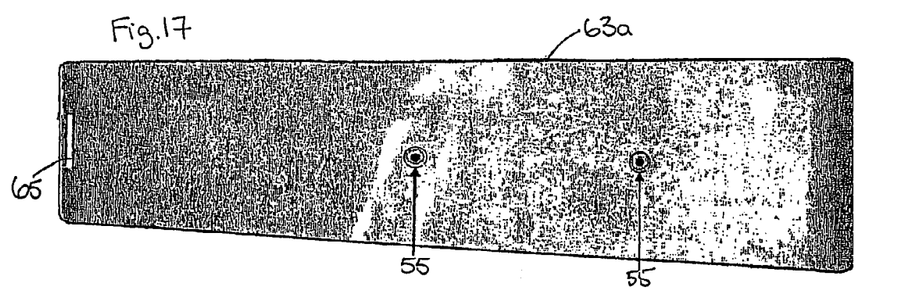
FIG. 17 is a bottom perspective of the harness protector according to FIG. 7.
Figure 18:
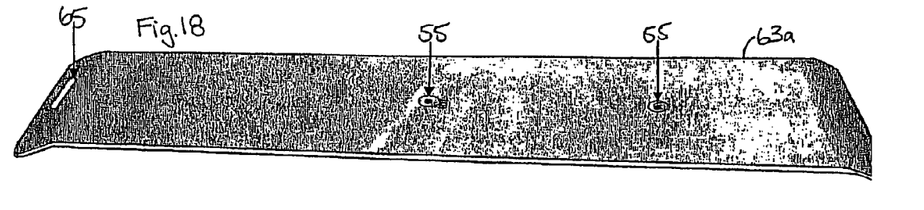
FIG. 18 is a side perspective view of the harness protector according to FIG. 7.
Figure 19:
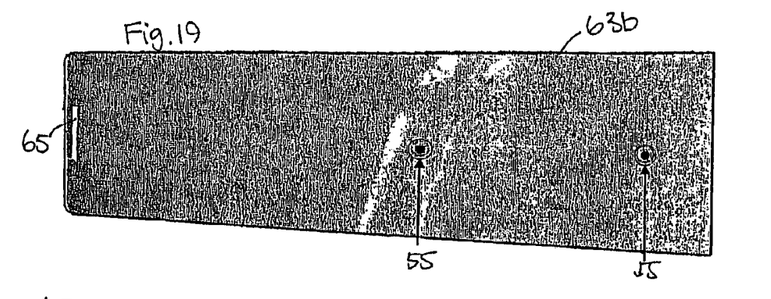
FIG. 19 is a bottom perspective view of the harness protector according FIG. 8.
Figure 20:
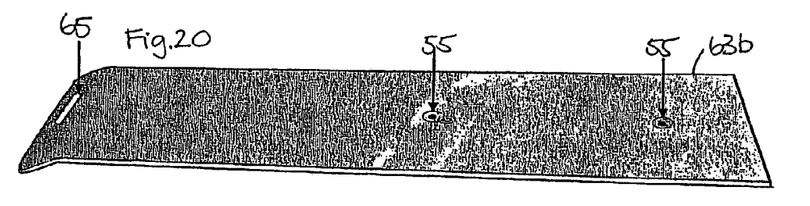
FIG. 20 is a side perspective view of the harness protector according to FIG. 8.
Figure 21:
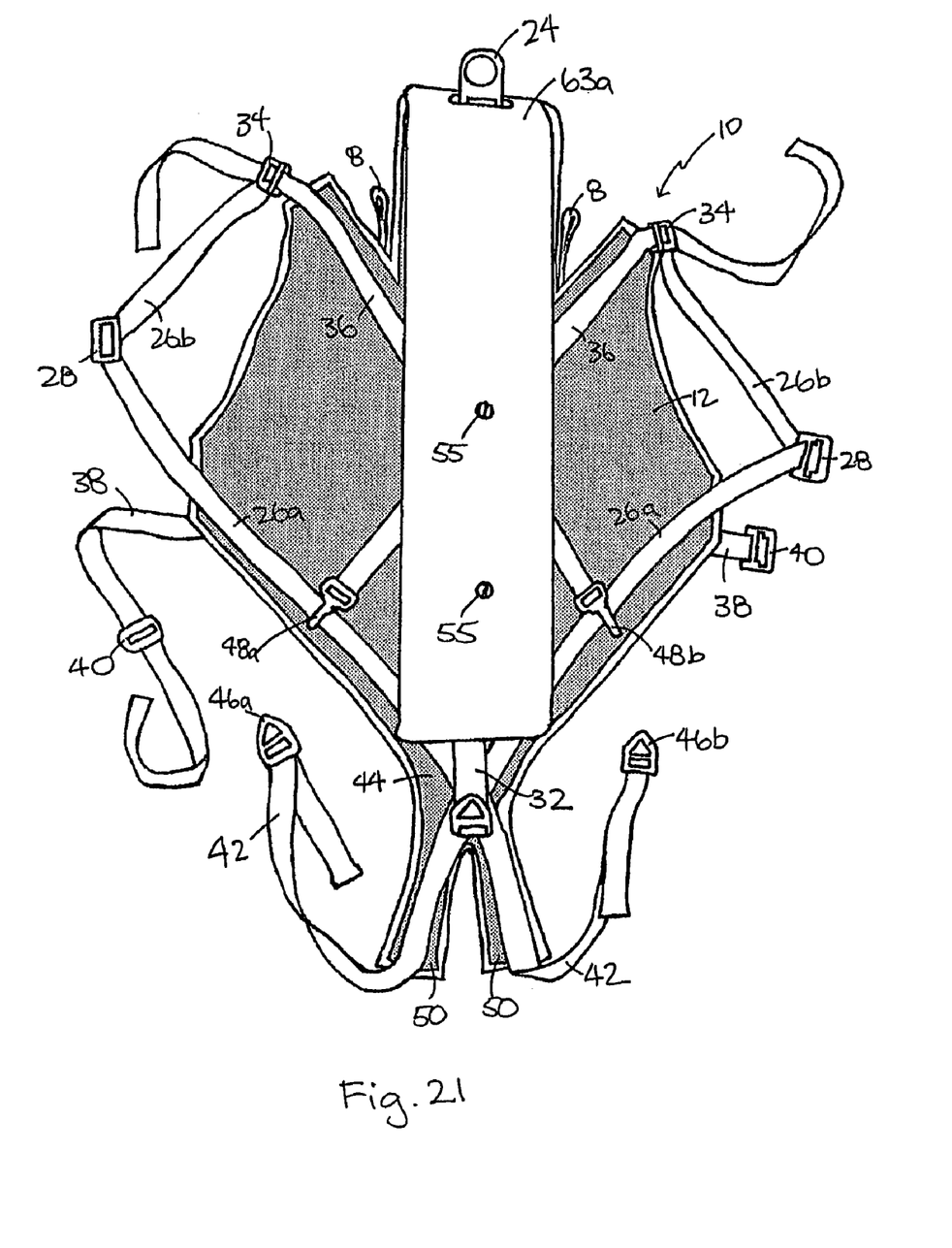
FIG. 21 is a bottom view of the harness protector according to FIG. 7 attached to the harness according to an embodiment of the invention.

FIGS. 7, 8, and 17 to 20 illustrate alternative embodiments of the harness protector of the invention. FIGS. 7, 17, and 18 illustrate a full length harness protector 63a, and FIGS. 8, 19, and 20 illustrate a shorter length harness protector 63b. Harness protectors 63a and 63b each comprise slots 65 for inserting lifting ring 24, and bolting holes 55 for attaching these harness protectors to harness 10. Harness protectors 63a and 63b are attached to back support 20 and mantle 12 by inserting fasteners through bolting holes 55, through grommet holes 52 of mantle 12, and fastening the fasteners to back support 20 at bolting points 54. FIG. 21 illustrates harness protector 63a attached to harness 10. Different sized harness protectors can be used, depending on the length of back support 20 used.

EXAMPLE

The following example describes how harness 10 can be used to affect a rescue of a patient. If a patient were injured and required extrication from a confined space, or a space which required the patient to be extricated vertically, such as found in barges, ships, tanks, tower cranes, structural collapses, crevices, or vehicles, emergency response personnel could affect the rescue of the patient by securing the patient into harness 10. If the patient had an injury which required immobilization of the patient's spine to prevent further injury, emergency response personnel could use harness 10 with back support 20 inserted into pocket 18, wherein the length of back support 20 is selected based on the restrictions of the space.

Harness 10 can be used without back support 20, which may facilitate rescues from confined spaces. However, if spinal immobilization is required, the patient's head can be secured to head support 14 using straps 16, which can be made of a flock and loop material, or other suitable material which can be easily attached and detached and adjusted to accommodate patients with different head sizes. When head support 14 is looped through tracks 56 of back support 20, it can be held in place along back support 20 due to friction between the material of head support 14 and straps 16 and back support 20. In an alternative embodiment, harness 10 can comprise a floating head support 14 which is slidably attached to back support 20 and allows a patient's head to move freely longitudinally, but does not does not allow the patient's head to rotate or move side to side.

Once the patient's head is secured, harness 10 can be secured around the patient's arms and torso by wrapping mantle 12 around the patient and securing chest straps 26 across the patient's chest by connecting floating fastener 28. Chest straps 26 can be tightened over the patient's chest by adjusting the positions of the chest strap buckles 34 along the straps. Chest straps 26 can also crossed over the patient's chest, and the crossing point secured with a fastener. Waist strap 38 can also be secured around the patient's waist and arms by connecting waist fastener 40. Waist strap 38 can be tightened around the patient's waist by moving waist fastener 40 along the length of waist strap 38 as needed. The patient's legs can be secured into harness 10 by connecting leg strap buckle 43a with leg strap leg strap connector 48a, and leg strap leg strap buckle 43b with leg strap leg strap connector 48b. Leg loops formed by leg straps 42 can be tightened by pulling ends of leg straps 42 through leg strap buckles 43a and 43b. Harness protector 62 or 63 may be pre-attached to harness 10 so that additional time and effort does not need to be used to secure the harness protector to harness 10.

Another method of securing the patient in the harness involves leaving one of the patient's arms out of harness to further reduce the patient's profile. If it is necessary to reduce the patient's profile, one arm could be placed over the patient's head to reduce the width of the patient. The harness can also be secured to the patient by applying it directly to the torso of patient and not encompassing the arms as injuries to the patient dictate.

If a vertical extrication of the patient is required, a life line can be connected to lifting ring 24 to lift the patient.

Although these examples discloses a sequence of events for securing harness 10 to a patient, other methods of securing harness 10 using a different sequence of events are also contemplated and would be appreciated by persons skilled in the art. For example, another sequence of events that a person skilled in the art could consider to be appropriate, depending on the nature of the patient's injuries and the environment that the patient is located in, would be to secure the waist strap of the harness to the patient first, then the leg straps, then the chest straps, and lastly the head support. The patient's injuries may dictate the sequence of harness attachments, and rescue personnel and others of skill in the art would appreciate that different sequences can be used in different situations to effect a safe and minimally uncomfortable rescue of a patient.

As will be apparent to those skilled in the art in the light of the foregoing disclosure, many alterations and modifications are possible in the practice of this invention without departing from the spirit or scope thereof. For example, while a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

LIST OF DRAWING REFERENCES

| | |
|---|---|
| 8 | lifting straps |
| 10 | rescue harness |
| 12 | mantle |
| 14 | head support |
| 16 | straps |
| 17 | slot for head support and straps |
| 18 | pocket |
| 20 | back support |
| 21 | fastener |
| 22 | closure |
| 23 | fastener receiver |
| 24 | lifting ring |
| 26 | chest straps |
| 28 | floating fastener |
| 30 | reinforcement straps |
| 32 | centre strap |
| 34 | chest strap buckles |
| 36 | reinforcement straps |
| 38 | waist strap |
| 40 | waist fastener |
| 42 | leg straps |
| 43 | leg strap buckles |
| 44 | y-shaped tail |
| 45 | lower lifting ring |
| 46 | lifting rings |
| 48 | leg strap connectors |
| 50 | branch of y-shaped tail |
| 52 | grommet |
| 54 | bolting point |
| 55 | bolting holes |
| 56 | head support track |
| 59 | backing of head support |
| 60 | projecting member of head support |
| 62 | harness protector |
| 63 | alternative embodiment of harness protector |
| 64 | lifting ring slot |
| 65 | lifting ring slot of alternative embodiment of harness protector |
| 66 | leg strap connector slots |
| 68 | lower slot |
| 70 | harness protector attachment means |

What is claimed is:

1. A rescue device comprising:
a floating head support slidably attached to a back support, the floating head support comprising one or more straps for securing a patient's head to the floating head support;
a mantle adapted to be wrapped around the person's arms and torso, the mantle having first and second sides extending outwardly on first and second sides of the back support respectively;
first and second chest straps extending from the mantle wherein first and second ends of the first chest strap are respectively attached to the first side of the mantle at spaced apart locations and first and second ends of the second chest strap are respectively attached to the second side of the mantle at spaced apart locations;
a fastener for securing the chest straps across the person's chest, the fastener having first and second portions detachably affixable to one another, the first portion slidable along a length of the first chest strap between the first and second ends of the first chest strap and the second portion slidable along a length of the second chest strap between the first and second ends of the second chest strap; and
a waist strap having first and second ends attached respectively to the first and second sides of the mantle, the waist strap comprising a releasable fastener operable to permit the waist strap to be tightened to pull the first and second sides of the mantle toward one another around the person's elbows.

2. A rescue device according to claim 1, wherein the back support comprises a track and the floating head support is slidably mounted to the track.

3. A rescue device according to claim 1, wherein the device is incorporated into a rescue harness.

4. A rescue device according to claim 3, comprising leg straps for forming leg loops for the patient's legs.

5. A rescue device according to claim 3, comprising one or more lifting rings for lifting the rescue harness.

6. A rescue device according to claim 3, comprising detachable harness protector comprising a sheet of abrasion-resistant material having at least one slot for receiving the harness and attaching to the harness.

7. A rescue device according to claim 1 further compromising:
a pocket in the mantle for carrying the back support;
one or more lifting rings for lifting the patient secured in the rescue device;
one or more straps attached to the mantle for attaching the one or more lifting rings to the rescue device; and
leg straps adapted to attach to the mantle, wherein the leg straps form leg loops for the patient's legs when the leg straps are attached to the mantle;
wherein, the one or more straps for attaching the lifting rings, and the leg loops formed by the leg straps support the weight of the patient when the patient is lifted in the rescue device.

8. A rescue device according to claim 7, wherein the pocket comprises one or more closures to accommodate back supports of different lengths.

9. A rescue device according to claim 7, wherein the back support comprises a track for slidably attaching the floating head support.

10. A rescue device according to claim 1 further comprising a removable harness protector containing at least one slot for receiving the harness and attaching to the harness.

11. A rescue device according to claim 1 further compromising:
a pocket in the mantle for carrying the back support;
one or more lifting rings for lifting the patient secured in the rescue device;
one or more straps attached to the mantle for attaching the lifting ring to the rescue device;
leg straps adapted to attach to the mantle, wherein the leg straps form leg loops for the patient's legs when the leg straps are attached to the mantle; and
a removable harness protector to protect the rescue device from abrasion, the harness protector comprising a sheet of abrasion-resistant material containing at least one slot for receiving at least one of the one or more lifting rings;
wherein, the one or more straps for attaching the one or more lifting rings, and leg loops formed by the leg straps support the weight of the patient when the patient is lifted in the rescue device.

12. A rescue device according to claim 11, wherein the pocket comprises one or more closures to accommodate back supports of different lengths.

13. A rescue device according to claim 11, wherein the back support comprises a track for slidably attaching the floating head support.

14. A rescue device according to claim 1, wherein the chest straps are adjustable in length.

* * * * *